(12) United States Patent
Kane et al.

(10) Patent No.: US 10,391,317 B2
(45) Date of Patent: Aug. 27, 2019

(54) SYSTEMS AND METHODS FOR CARDIO-RESPIRATORY PACING

(71) Applicant: Cardiac Pacemakers, Inc., St. Paul, MN (US)

(72) Inventors: Michael J. Kane, Roseville, MN (US); Allan Charles Shuros, St. Paul, MN (US); Paul Huelskamp, St. Paul, MN (US); Benjamin J. Haasl, Forest Lake, MN (US); Keith R. Maile, New Brighton, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 12 days.

(21) Appl. No.: 15/249,050

(22) Filed: Aug. 26, 2016

(65) Prior Publication Data

US 2017/0056669 A1  Mar. 2, 2017

Related U.S. Application Data

(60) Provisional application No. 62/211,377, filed on Aug. 28, 2015.

(51) Int. Cl.
*A61N 1/36* (2006.01)
*A61N 1/365* (2006.01)
*A61N 1/375* (2006.01)
*A61N 1/362* (2006.01)

(52) U.S. Cl.
CPC ..... *A61N 1/36585* (2013.01); *A61N 1/36514* (2013.01); *A61N 1/36521* (2013.01); *A61N 1/36535* (2013.01); *A61N 1/36542* (2013.01); *A61N 1/3756* (2013.01); *A61N 1/362* (2013.01); *A61N 1/3611* (2013.01)

(58) Field of Classification Search
CPC .............. A61N 1/36535; A61N 1/36595
See application file for complete search history.

(56) References Cited

U.S. PATENT DOCUMENTS

| | | |
|---|---|---|
| 5,003,976 A | 4/1991 | Alt |
| 6,371,922 B1 | 4/2002 | Baumann et al. |
| 6,574,507 B1 | 6/2003 | Bonnet |
| 6,640,135 B1 | 10/2003 | Salo et al. |
| 7,302,295 B2 | 11/2007 | Stahmann et al. |

(Continued)

OTHER PUBLICATIONS

International Search Report and Written Opinion for Application No. PCT/US2016/049078, 12 pages, dated Dec. 12, 2016.

*Primary Examiner* — Eric D. Bertram
(74) *Attorney, Agent, or Firm* — Seager, Tufte & Wickhem LLP

(57) ABSTRACT

Systems, devices, and methods for pacing a heart of a patient are disclosed. In some embodiments, a method for pacing a patient's heart may include determining a posture of the patient and determining if the determined posture corresponds to a predetermined sleep posture. If the determined posture correspond to the predetermined sleep posture, the method may further comprise determining a respiration phase of the patient and pacing the patient's heart at a pacing rate that is modulated based on the determined respiration phase of the patient. If the determined posture does not correspond to the predetermined sleep posture, the method may pace the patient's heart at a pacing rate that is not dependent on the respiration phase of the patient.

13 Claims, 12 Drawing Sheets

(56) References Cited

U.S. PATENT DOCUMENTS

| | | |
|---|---|---|
| 7,343,199 B2 | 3/2008 | Hatlestad et al. |
| 7,467,012 B1 | 12/2008 | Park et al. |
| 7,904,156 B2 | 3/2011 | Maskara et al. |
| 7,904,158 B2 | 3/2011 | Stegemann et al. |
| 8,103,343 B2 | 1/2012 | Hopper et al. |
| 8,290,587 B2 | 10/2012 | Maskara et al. |
| 8,463,380 B2 | 6/2013 | Hopper et al. |
| 8,761,879 B2 | 6/2014 | Hopper et al. |
| 2008/0234556 A1 | 9/2008 | Brook et al. |
| 2008/0275520 A1 | 11/2008 | Hopper et al. |
| 2010/0312301 A1 | 12/2010 | Stahmann |
| 2012/0101393 A1* | 4/2012 | Zhang ............... A61B 5/0452 600/484 |
| 2012/0130443 A1 | 5/2012 | Hopper et al. |
| 2012/0290032 A1* | 11/2012 | Cho ................... A61N 1/056 607/20 |
| 2013/0274821 A1 | 10/2013 | Hopper et al. |
| 2014/0350626 A1 | 11/2014 | Mower |
| 2014/0371519 A1 | 12/2014 | Spence et al. |
| 2016/0114169 A1* | 4/2016 | Sheldon ............. A61N 1/3704 607/17 |

\* cited by examiner

SYSTEMS AND METHODS FOR CARDIO-RESPIRATORY PACING

CROSS REFERENCE TO RELATED APPLICATIONS

This application claims the benefit of U.S. Provisional Patent Application Ser. No. 62/211,377 filed on Aug. 28, 2015, the disclosure of which is incorporated herein by reference.

TECHNICAL FIELD

The present disclosure generally relates to systems, devices, and methods for delivering pacing therapy to a patient, and more particularly, to systems, devices, and methods for modulating pacing therapy based on a respiration phase of the patient.

BACKGROUND

Pacing instruments can be used to treat patients suffering from various heart conditions that result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) are often implanted in a patient's body. Such devices may monitor and provide electrical stimulation to the heart to help the heart operate in a more normal, efficient and/or safe manner. In some cases, such devices may modulate delivered pacing therapy based on patient related characteristics.

SUMMARY

The present disclosure generally relates to systems, devices, and methods for delivering pacing therapy to a patient, and more particularly, to systems, devices, and methods for modulating pacing therapy based on a respiration phase of the patient.

In a first illustrative embodiment, a method for pacing a patient's heart may comprise determining a posture of the patient and determining if the sensed posture corresponds to a predetermined sleep posture. If the sensed posture does correspond to a predetermined sleep posture, the method may further comprise determining a respiration phase of the patient and pacing the patient's heart at a pacing rate that is modulated based on the determined respiration phase of the patient. If, however, the sensed posture does not correspond to a predetermined sleep posture, the method may pace the patient's heart at a pacing rate that is not dependent on the respiration phase of the patient.

Additionally, or alternatively, to the first illustrative embodiment, the posture of the patient may be determined at least in part using an accelerometer.

Additionally, or alternatively, in any of the above embodiments with respect to the first illustrative embodiment, the respiration phase of the patient may be determined based at least in part on a signal generated by an accelerometer.

Additionally, or alternatively, in any of the above embodiments with respect to the first illustrative embodiment, the respiration phase of the patient may be determined based at least in part on a measure related to a transthoracic impedance of the patient.

Additionally, or alternatively, in any of the above embodiments with respect to the first illustrative embodiment, the respiration phase of the patient may be determined based at least in part on a measure related to an intracardiac impedance of the patient.

Additionally, or alternatively, in any of the above embodiments with respect to the first illustrative embodiment, the respiration phase of the patient may be determined based at least in part on a measure sensed by a flow sensor.

Additionally, or alternatively, in any of the above embodiments with respect to the first illustrative embodiment, the respiration phase of the patient may be determined based at least in part on a measure sensed by a pressure sensor.

Additionally, or alternatively, in any of the above embodiments with respect to the first illustrative embodiment, the respiration phase of the patient may be sensed at discrete sensing events and then predicted between the discrete sensing events.

Additionally, or alternatively, in any of the above embodiments with respect to the first illustrative embodiment, the method may further comprise modulating a lower rate limit (LRL) of the pacing rate based on the determined respiration phase of the patient if the sensed posture corresponds to the predetermined sleep posture.

Additionally, or alternatively, in any of the above embodiments with respect to the first illustrative embodiment, the pacing may be performed by a leadless cardiac pacemaker.

Additionally, or alternatively, in any of the above embodiments with respect to the first illustrative embodiment, sensing the posture of the patient may be performed by the leadless cardiac pacemaker.

Additionally, or alternatively, in any of the above embodiments with respect to the first illustrative embodiment, determining if the sensed posture does or does not correspond to the predetermined sleep posture may be performed by the leadless cardiac pacemaker.

Additionally, or alternatively, in any of the above embodiments with respect to the first illustrative embodiment, determining the respiration phase of the patient may be performed by a leadless cardiac pacemaker.

In a second illustrative embodiment, a method for pacing a patient's heart with a leadless cardiac pacemaker may comprise determining, by the leadless cardiac pacemaker, if a current posture of the patient corresponds to a predetermined sleep posture. If the current posture of the patient corresponds to a predetermined sleep posture, the method may further comprise receiving, by the leadless cardiac pacemaker, a signal indicative of a respiration pattern of a patient and modulating a rate of delivery of electrical stimulation pulses to the patient's heart based at least in part on the signal indicative of the respiration pattern.

Additionally, or alternatively, the second illustrative embodiment may further comprise determining periods of inhalation and periods of exhalation based at least in part on the received signal indicative of the respiration pattern.

Additionally, or alternatively, to any of the above embodiments with respect to the second illustrative embodiment, modulating the rate of delivery of electrical stimulation pulses based at least in part on the signal indicative of the respiration pattern may comprise delivering electrical stimulation pulses at different rates during periods of inhalation and periods of exhalation.

Additionally, or alternatively, to any of the above embodiments with respect to the second illustrative embodiment, the rate of delivery of electrical stimulation pulses during periods of exhalation may be between about 1 pulse per minute to about 3 pulses per minute slower than during periods of inhalation.

Additionally, or alternatively, to any of the above embodiments with respect to the second illustrative embodiment, the signal indicative of the respiration pattern may be generated by an accelerometer of the leadless cardiac pacemaker.

Additionally, or alternatively, to any of the above embodiments with respect to the second illustrative embodiment, the signal indicative of the respiration pattern may be generated by a device external to the leadless cardiac pacemaker and communicated to the leadless cardiac pacemaker In a third illustrative embodiment, a leadless cardiac pacemaker (LCP) for delivering electrical stimulation pulses to a heart of a patient may comprise a plurality of electrodes and a controller connected to the plurality of electrodes. In some embodiments, the controller may be configured to determine periods of inhalation and periods of exhalation of the patient, deliver electrical stimulation pulses to the heart of the patient via the plurality of electrodes, and modulate a rate of delivery of the electrical stimulation pulses via the plurality of electrodes based at least in part on the determined periods of inhalation and periods of exhalation.

Additionally, or alternatively, to the third illustrative embodiment, the controller may further be configured to determine a current posture of a patient and to determine if the current posture corresponds to a predetermined sleep posture. If the current posture of the patient corresponds to a predetermined sleep posture, the controller may further be configured to determine periods of inhalation and periods of exhalation of the patient, deliver electrical stimulation pulses to the heart of the patient via the plurality of electrodes, and modulate a rate of delivery of the electrical stimulation pulses via the plurality of electrodes based at least in part on the determined periods of inhalation and periods of exhalation. If the current posture does not correspond to a predetermined sleep posture, the controller may be configured to pace the patient's heart at a pacing rate that is not dependent on the periods of inhalation and periods of exhalation of the patient.

In a fourth illustrative embodiment, a medical device may comprise a plurality of electrodes and a controller connected to the plurality of electrodes. In some embodiments, the controller may be controller configured to: determine a posture of a patient, and determine if the sensed posture corresponds to a predetermined sleep posture. If the sensed posture does correspond to the predetermined sleep posture, the controller may be further configured to: determine a respiration phase and apply pacing pulses to the plurality of electrodes at a pacing rate that is modulated based on the determined respiration phase. If the sensed orientation does not correspond to the predetermined sleep posture, the controller may be further configured to: apply pacing pulses to the plurality of electrodes at a pacing rate that is not dependent on the determined respiration phase.

Additionally, or alternatively, to the fourth illustrative embodiment, the posture of the patient may be determined at least in part using an accelerometer.

Additionally, or alternatively, in any of the above embodiments with respect to the fourth illustrative embodiment, the respiration phase may be determined based at least in part on a signal generated by an accelerometer.

Additionally, or alternatively, in any of the above embodiments with respect to the fourth illustrative embodiment, the respiration phase may be determined based at least in part on a measure related to a sensed transthoracic impedance.

Additionally, or alternatively, in any of the above embodiments with respect to the fourth illustrative embodiment, the respiration phase of the patient may be determined based at least in part on a measure related to an intracardiac impedance of the patient.

Additionally, or alternatively, in any of the above embodiments with respect to the fourth illustrative embodiment, the respiration phase may be determined based at least in part on a measure sensed by a flow sensor.

Additionally, or alternatively, in any of the above embodiments with respect to the fourth illustrative embodiment, the respiration phase may be determined based at least in part on a measure sensed by a pressure sensor.

Additionally, or alternatively, in any of the above embodiments with respect to the fourth illustrative embodiment, the respiration phase may be sensed at discrete sensing events and then predicted between the discrete sensing events.

Additionally, or alternatively, in any of the above embodiments with respect to the fourth illustrative embodiment, the controller may be further configured to modulate a lower rate limit (LRL) of the pacing rate based on the determined respiration phase if the sensed orientation corresponds to the predetermined sleep posture.

Additionally, or alternatively, in any of the above embodiments with respect to the fourth illustrative embodiment, the medical device may be a leadless cardiac pacemaker.

Additionally, or alternatively, in any of the above embodiments with respect to the fourth illustrative embodiment, to determine the posture, the controller may be configured to receive an indication of the posture from a device external to the medical device.

Additionally, or alternatively, in any of the above embodiments with respect to the fourth illustrative embodiment, to determine if the sensed posture does or does not correspond to the predetermined sleep posture, the controller may be configured to receive an indication as to whether the sensed posture does or does not correspond to the predetermined sleep posture from a device external to the medical device.

Additionally, or alternatively, in any of the above embodiments with respect to the fourth illustrative embodiment, to determine the respiration phase of the patient, the controller may be configured to receive an indication of the respiration phase from a device external to the medical device.

In a fifth illustrative embodiment, a leadless cardiac pacemaker (LCP) may comprise a plurality of electrodes and a controller connected to the plurality of electrodes. In some embodiments, the controller may be configured to determine periods of inhalation and periods of exhalation of a patient, apply electrical stimulation pulses to the plurality of electrodes, and modulate a rate of delivery of the electrical stimulation pulses via the plurality of electrodes based at least in part on the determined periods of inhalation and periods of exhalation.

Additionally, or alternatively, in the fifth illustrative embodiment, the controller may be further configured to determine a current posture of a patient and to determine if the current posture corresponds to a predetermined sleep posture, and if so: determine periods of inhalation and periods of exhalation of the patient, apply electrical stimulation pulses to the plurality of electrodes, and modulate a rate of delivery of the electrical stimulation pulses to the plurality of electrodes based at least in part on the determined periods of inhalation and periods of exhalation. If the current posture does not correspond to a predetermined sleep posture, the controller may be configured to apply pacing pulses to the plurality of electrodes at a pacing rate that is not dependent on the determined periods of inhalation and periods of exhalation.

Additionally, or alternatively, in any of the above embodiments with respect to the fifth illustrative embodiment, the controller may be further configured to determine periods of inhalation and periods of exhalation of the patient using an accelerometer signal.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
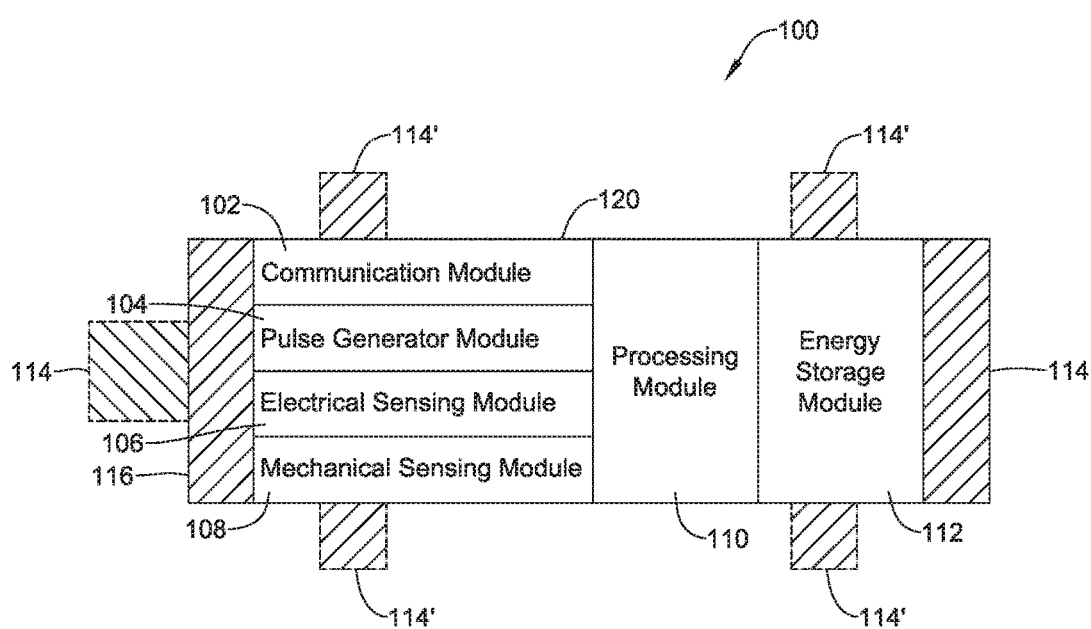
FIG. 1 is a schematic block diagram of an illustrative leadless cardiac pacemaker (LCP) according to one embodiment of the present disclosure.

While the disclosure is amenable to various modifications and alternative forms, specifics thereof have been shown by way of embodiment in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

This disclosure describes systems, devices, and methods for modifying delivery of pacing pulses according to a respiration pattern of a patient. For example, devices of the present disclosure may be configured to determine a respiration pattern of a patient. The devices may then adjust the rate of delivery of pacing pulses in accordance with the determined respiration rate. As one example, the devices may slow the delivery rate of pacing pulses during periods of exhalation relative to a delivery rate of pacing pulses during periods of inhalation.

FIG. 1 is a conceptual schematic block diagram of an exemplary leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 1, LCP 100 may be a compact device with all components housed within LCP 100 or directly on housing 120. In some instances, LCP 100 may include communication module 102, pulse generator module 104, electrical sensing module 106, mechanical sensing module 108, processing module 110, energy storage module 112, and electrodes 114.

As depicted in FIG. 1, LCP 100 may include electrodes 114, which can be secured relative to housing 120 and electrically exposed to tissue and/or blood surrounding LCP 100. Electrodes 114 may generally conduct electrical signals to and from LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, an insulative material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120. As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication signals and/or electrical stimulation pulses, and/or may sense intrinsic cardiac electrical signals, communication signals, and/or electrical stimulation pulses.

Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length. As used herein, the length is a dimension of electrodes 114 and/or 114' that extends away from the outer surface of the housing 120. In some instances, at least some of electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. Communication module 102 may additionally be configured to sense for communication signals delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may be communicating with other devices via conducted signals, radio frequency (RF) signals, optical signals, acoustic signals, inductive coupling, and/or any other suitable communication methodology. Where communication module 102 generates electrical communication signals, communication module 102 may include one or more capacitor elements and/or other charge storage devices to aid in generating and delivering communication signals. In the embodiment shown, communication module 102 may use energy stored in energy storage module 112 to generate the communication signals. In at least some examples, communication module 102 may include a switching circuit that is connected to energy storage module 112 and, with the switching circuitry, may connect energy storage module 112 to one or more of electrodes 114/114' to generate the communication signals.

As shown in FIG. 1, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, LCP 100 may vary the rate at which pulse generator module 104 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. When used to treat other ailments, the pulse generator module 104 may generate electrical stimulation pulses suitable for neurostimulation therapy or the like. Pulse generator module 104 may include one or more capacitor elements and/or other charge storage devices to aid in generating and delivering appropriate electrical stimulation pulses. In at least some embodiments, pulse generator module 104 may use energy stored in energy storage module 112 to generate the electrical stimulation pulses. In some particular embodiments, pulse generator module 104 may include a switching circuit that is connected to energy storage module 112 and may connect energy storage module 112 to one or more of electrodes 114/114' to generate electrical stimulation pulses.

LCP 100 may further include an electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114' via a sensor amplifier or the like. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, including multi-axis accelerometers such as two- or three-axis accelerometers, gyroscopes, including multi-axis gyroscopes such as two- or three-axis gyroscopes, blood pressure sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters. Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module. In at least some examples, LCP 100 may only include one of electrical sensing module 106 and mechanical sensing module 108. In some cases, any combination of the processing module 110, electrical sensing module 106, mechanical sensing module 108, communication module 102, pulse generator module 104 and/or energy storage module may be considered a controller of the LCP 100.

Processing module 110 may be configured to direct the operation of LCP 100 and may, in some embodiments, be termed a controller. For example, processing module 110 may be configured to receive cardiac electrical signals from electrical sensing module 106 and/or physiological signals from mechanical sensing module 108. Based on the received signals, processing module 110 may determine, for example, occurrences and types of arrhythmias and other determinations such as whether LCP 100 has become dislodged. Processing module 110 may further receive information from communication module 102. In some embodiments, processing module 110 may additionally use such received information to determine occurrences and types of arrhythmias and/or and other determinations such as whether LCP 100 has become dislodged. In still some additional embodiments, LCP 100 may use the received information instead of the signals received from electrical sensing module 106 and/or mechanical sensing module 108—for instance if the received information is deemed to be more accurate than the signals received from electrical sensing module 106 and/or mechanical sensing module 108 or if electrical sensing module 106 and/or mechanical sensing module 108 have been disabled or omitted from LCP 100.

After determining an occurrence of an arrhythmia, processing module 110 may control pulse generator module 104 to generate electrical stimulation pulses in accordance with one or more electrical stimulation therapies to treat the determined arrhythmia. For example, processing module 110 may control pulse generator module 104 to generate pacing pulses with varying parameters and in different sequences to effectuate one or more electrical stimulation therapies. As one example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, processing module 110 may monitor one or more physiological parameters of the patient which may indicate a need for an increased heart rate (e.g. due to increased metabolic demand). Processing module 110 may then increase the rate at which pulse generator module 104 generates electrical stimulation pulses. Adjusting the rate of delivery of the electrical stimulation pulses based on the one or more physiological parameters may extend the battery life of LCP 100 by only requiring higher rates of delivery of electrical stimulation pulses when the physiological parameters indicate there is a need for increased cardiac output. Additionally, adjusting the rate of delivery of the electrical stimulation pulses may increase a comfort level of the patient by more closely matching the rate of delivery of electrical stimulation pulses with the cardiac output need of the patient.

For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, processing module 110 may control pulse generator module 104 to reduce the rate of delivered pacing pulses down to a safer level. In CRT, processing module 110 may control pulse generator module 104 to deliver pacing pulses in coordination with another device to cause the heart to contract more efficiently. In cases where pulse generator module 104 is capable of generating defibrillation and/or cardioversion pulses for defibrillation/cardioversion therapy, processing module 110 may control pulse generator module 104 to generate such defibrillation and/or cardioversion pulses. In some cases, processing module 110 may control pulse generator module 104 to generate electrical stimulation pulses to provide electrical stimulation therapies different than those examples described above.

Aside from controlling pulse generator module 104 to generate different types of electrical stimulation pulses and in different sequences, in some embodiments, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may help LCP 100 provide more effective delivery of electrical stimulation therapy.

In some embodiments, processing module 110 may further control communication module 102 to send information to other devices. For example, processing module 110 may control communication module 102 to generate one or more communication signals for communicating with other devices of a system of devices. For instance, processing module 110 may control communication module 102 to generate communication signals in particular pulse sequences, where the specific sequences convey different information. Communication module 102 may also receive communication signals for potential action by processing module 110.

In further embodiments, processing module 110 may control switching circuitry by which communication module 102 and pulse generator module 104 deliver communication signals and/or electrical stimulation pulses to tissue of the patient. As described above, both communication module 102 and pulse generator module 104 may include circuitry for connecting one or more electrodes 114 and/114' to communication module 102 and/or pulse generator module 104 so those modules may deliver the communication signals and electrical stimulation pulses to tissue of the patient. The specific combination of one or more electrodes by which communication module 102 and/or pulse generator module 104 deliver communication signals and electrical stimulation pulses may influence the reception of communication signals and/or the effectiveness of electrical stimulation pulses. Although it was described that each of communication module 102 and pulse generator module 104 may include switching circuitry, in some embodiments, LCP 100 may have a single switching module connected to the communication module 102, the pulse generator module 104, and electrodes 114 and/or 114'. In such embodiments, processing module 110 may control the switching module to connect modules 102/104 and electrodes 114/114' as appropriate.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip. In still other embodiments, processing module 110 may not be a single component. For example, processing module 110 may include multiple components positioned at disparate locations within LCP 100 in order to perform the various described functions. For example, certain functions may be performed in one component of processing module 110, while other functions are performed in a separate component of processing module 110.

Processing module 110, in additional embodiments, may include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110, may be volatile memory, non-volatile memory, or a combination of volatile memory and non-volatile memory.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. In still other embodiments, energy storage module 112 may include other types of energy storage devices such as capacitors or super capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, anchor 116 may include other structures such as barbs, spikes, or the like to facilitate engagement with the surrounding cardiac tissue.

In some examples, LCP 100 may be configured to be implanted on a patient's heart or within a chamber of the patient's heart. For instance, LCP 100 may be implanted within any of a left atrium, right atrium, left ventricle, or right ventricle of a patient's heart. By being implanted within a specific chamber, LCP 100 may be able to sense cardiac electrical signals originating or emanating from the specific chamber that other devices may not be able to sense with such resolution. Where LCP 100 is configured to be implanted on a patient's heart, LCP 100 may be configured to be implanted on or adjacent to one of the chambers of the heart, or on or adjacent to a path along which intrinsically generated cardiac electrical signals generally follow. In these examples, LCP 100 may also have an enhanced ability to sense localized intrinsic cardiac electrical signals and deliver localized electrical stimulation therapy. In embodiments where LCP 100 includes an accelerometer, LCP 100 may additionally be able to sense the motion of the cardiac wall to which LCP 100 is attached.

Figure 2:
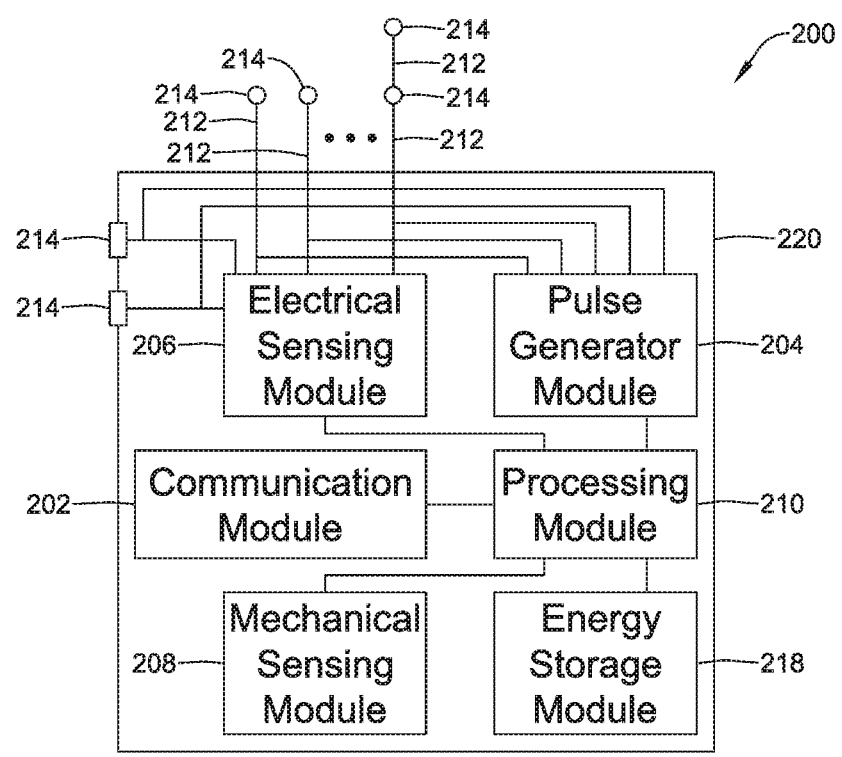
FIG. 2 is a schematic block diagram of another illustrative medical device that may be used in conjunction with the LCP of FIG. 1.

FIG. 2 depicts an embodiment of another device, medical device (MD) 200, which may operate to sense physiological signals and parameters and deliver one or more types of electrical stimulation therapy to tissues of the patient. In the embodiment shown, MD 200 may include a communication module 202, a pulse generator module 204, an electrical sensing module 206, a mechanical sensing module 208, a processing module 210, and an energy storage module 218. Each of modules 202, 204, 206, 208, and 210 may be similar to modules 102, 104, 106, 108, and 110 of LCP 100. Additionally, energy storage module 218 may be similar to energy storage module 112 of LCP 100. However, in some embodiments, MD 200 may have a larger volume within housing 220. In such embodiments, MD 200 may include a larger energy storage module 218 and/or a larger processing module 210 capable of handling more complex operations than processing module 110 of LCP 100.

While MD 200 may be another leadless device such as shown in FIG. 1, in some instances MD 200 may include leads, such as leads 212. Leads 212 may include electrical wires that conduct electrical signals between electrodes 214 and one or more modules located within housing 220. In some cases, leads 212 may be connected to and extend away from housing 220 of MD 200. In some embodiments, leads 212 are implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart. The electrodes 214 may conduct intrinsically generated electrical cardiac signals to leads 212. Leads 212 may, in turn, conduct the received electrical cardiac signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical stimulation signals to the cardiac tissue of the patient (either directly or indirectly). MD 200 may also include one or more electrodes 214 not disposed on a lead 212. For example, one or more electrodes 214 may be connected directly to housing 220.

Leads 212, in some embodiments, may additionally contain one or more sensors, such as accelerometers, blood pressure sensors, heart sound sensors, blood-oxygen sensors, and/or other sensors which are configured to measure one or more physiological parameters of the heart and/or patient. In such embodiments, mechanical sensing module 208 may be in electrical communication with leads 212 and may receive signals generated from such sensors.

While not required, in some embodiments MD 200 may be an implantable medical device. In such embodiments, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body. In such embodiments, leads 212 may be implanted at one or more various locations within the patient, such as within the heart of the patient, adjacent to the heart of the patient, adjacent to the spine of the patient, or any other desired location.

In some embodiments, MD 200 may be an implantable cardiac pacemaker (ICP). In these embodiments, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some embodiments, MD 200 may additionally be configured to provide defibrillation/cardioversion therapy.

In some instances, MD 200 may be an implantable cardioverter-defibrillator (ICD). In such embodiments, MD 200 may include one or more leads implanted within a patient's heart. MD 200 may also be configured to sense electrical cardiac signals, determine occurrences of tachyarrhythmias based on the sensed electrical cardiac signals, and deliver defibrillation and/or cardioversion therapy in response to determining an occurrence of a tachyarrhythmia (for example by delivering defibrillation and/or cardioversion pulses to the heart of the patient). In other embodiments, MD 200 may be a subcutaneous implantable cardioverter-defibrillator (SICD). In embodiments where MD 200 is an SICD, one of leads 212 may be a subcutaneously implanted lead. In at least some embodiments where MD 200 is an SICD, MD 200 may include only a single lead which is implanted subcutaneously but outside of the chest cavity, however this is not required.

In some embodiments, MD 200 may not be an implantable medical device. Rather, MD 200 may be a device external to the patient's body, and electrodes 214 may be skin-electrodes that are placed on a patient's body. In such embodiments, MD 200 may be able to sense surface electrical signals (e.g. electrical cardiac signals that are generated by the heart or electrical signals generated by a device implanted within a patient's body and conducted through the body to the skin). MD 200 may further be configured to deliver various types of electrical stimulation therapy, including, for example, defibrillation therapy via skin-electrodes 214.

Figure 3:
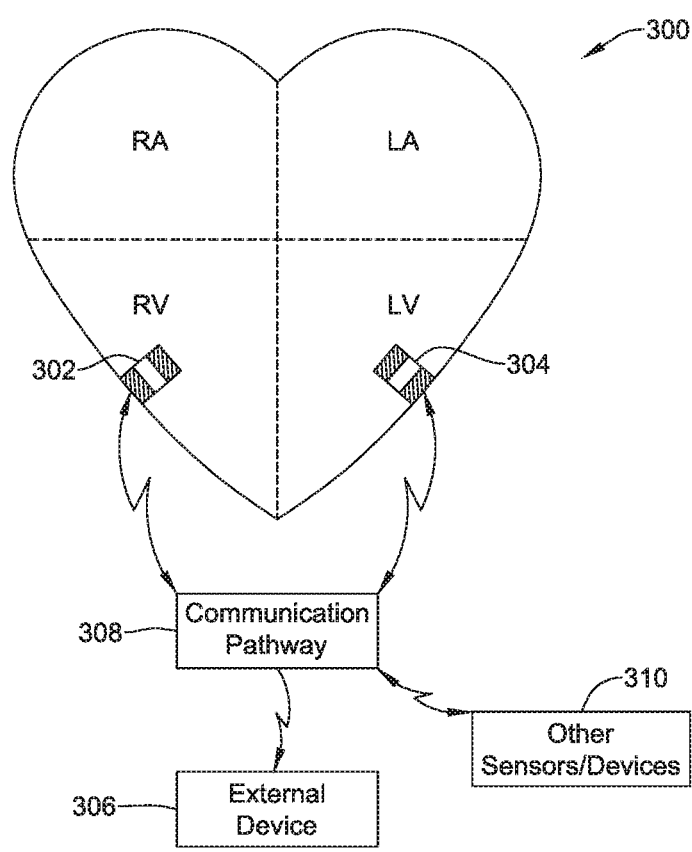
FIG. 3 is a schematic diagram of an exemplary medical system that includes multiple LCPs and/or other devices in communication with one another.

FIG. 3 illustrates an embodiment of a medical device system and a communication pathway through which multiple medical devices 302, 304, 306, and/or 310 of the medical device system may communicate. In the embodiment shown, medical device system 300 may include LCPs 302 and 304, external medical device 306, and other sensors/devices 310. External device 306 may be a device disposed external to a patient's body, as described previously with respect to MD 200. In at least some examples, external device 306 may represent an external support device such as a device programmer, as will be described in more detail below. Other sensors/devices 310 may be any of the devices described previously with respect to MD 200, such as ICPs, ICDs, and SICDs. Other sensors/devices 310 may also include various diagnostic sensors that gather information about the patient, such as accelerometers, blood pressure sensors, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one embodiment, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. One or more of devices 302/304, 306, and 310 of system 300 may additionally communicate command or response messages via communication pathway 308. The command messages may cause a receiving device to take a particular action whereas response messages may include requested information or a confirmation that a receiving device did, in fact, receive a communicated message or data.

It is contemplated that the various devices of system 300 may communicate via pathway 308 using RF signals, inductive coupling, optical signals, acoustic signals, or any other signals suitable for communication. Additionally, in at least some embodiments, the various devices of system 300 may communicate via pathway 308 using multiple signal types. For instance, other sensors/device 310 may communicate with external device 306 using a first signal type (e.g. RF communication) but communicate with LCPs 302/304 using a second signal type (e.g. conducted communication). Further, in some embodiments, communication between devices may be limited. For instance, as described above, in some embodiments, LCPs 302/304 may communicate with external device 306 only through other sensors/devices 310, where LCPs 302/304 send signals to other sensors/devices 310, and other sensors/devices 310 relay the received signals to external device 306.

In some cases, the various devices of system 300 may communicate via pathway 308 using conducted communication signals. Accordingly, devices of system 300 may have components that allow for such conducted communication. For instance, the devices of system 300 may be configured to transmit conducted communication signals (e.g. a voltage and/or current waveform punctuated with current and/or voltage pulses, referred herein as electrical communication pulses) into the patient's body via one or more electrodes of a transmitting device, and may receive the conducted communication signals via one or more electrodes of a receiving device. The patient's body may "conduct" the conducted communication signals from the one or more electrodes of the transmitting device to the electrodes of the receiving device in the system 300. In such embodiments, the delivered conducted communication signals may differ from pacing pulses, defibrillation and/or cardioversion pulses, or other electrical stimulation therapy signals. For example, the devices of system 300 may deliver electrical communication pulses at an amplitude/pulse width that is sub-threshold. That is, the communication pulses have an amplitude/pulse width designed to not capture the heart. In some cases, the amplitude/pulse width of the delivered electrical communication pulses may be above the capture threshold of the heart, but may be delivered during a refractory period of the heart and/or may be incorporated in or modulated onto a pacing pulse, if desired.

Additionally, unlike normal electrical stimulation therapy pulses, the electrical communication pulses may be delivered in specific sequences which convey information to receiving devices. For instance, delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, a predefined sequence of communication pulses may represent a corresponding symbol (e.g. a logic "1" symbol, a logic "0" symbol, an ATP therapy trigger symbol, etc.). In some cases, conducted communication pulses may be voltage pulses, current pulses, biphasic voltage pulses, biphasic current pulses, or any other suitable electrical pulse as desired.

Figure 4:
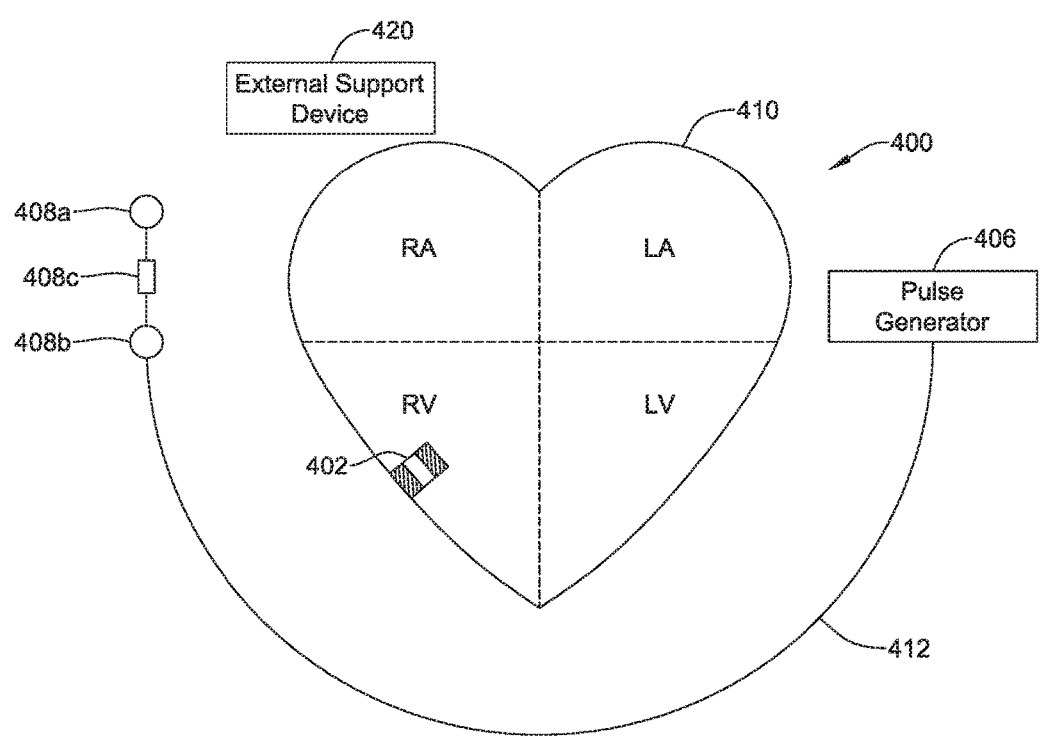
FIG. 4 is a schematic diagram of a system including an LCP and another medical device, in accordance with another embodiment of the present disclosure.

FIG. 4 depicts an illustrative medical device system 400 that may be configured to operate together. For example, system 400 may include multiple devices that are implanted within a patient and are configured to sense physiological signals, determine occurrences of cardiac arrhythmias, and deliver electrical stimulation to treat detected cardiac arrhythmias. In some embodiments, the devices of system 400 may be configured to determine occurrences of dislodgment of one or more devices of system 400. In FIG. 4, an LCP 402 is shown fixed to the interior of the right ventricle of the heart 410, and a pulse generator 406 is shown coupled to a lead 412 having one or more electrodes 408a-408c. In some cases, pulse generator 406 may be part of a subcutaneous implantable cardioverter-defibrillator (SICD), and the one or more electrodes 408a-408c may be positioned subcutaneously adjacent the heart. LCP 402 may communicate with the SICD, such as via communication pathway 308. The locations of LCP 402, pulse generator 406, lead 412, and electrodes 408a-c depicted in FIG. 4 are just exemplary. In other embodiments of system 400, LCP 402 may be positioned in the left ventricle, right atrium, or left atrium of the heart, as desired. In still other embodiments, LCP 402 may be implanted externally adjacent to heart 410 or even remote from heart 410.

Medical device system 400 may also include external support device 420. External support device 420 can be used to perform functions such as device identification, device programming and/or transfer of real-time and/or stored data between devices using one or more of the communication techniques described herein, or other functions involving communication with one or more devices of system 400. As one example, communication between external support device 420 and pulse generator 406 can be performed via a wireless mode, and communication between pulse generator 406 and LCP 402 can be performed via a conducted communication mode. In some embodiments, communication between LCP 402 and external support device 420 is accomplished by sending communication information through pulse generator 406. However, in other embodiments, communication between the LCP 402 and external support device 420 may be via a communication module.

FIG. 4 only illustrates one example embodiment of a medical device system that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs with or without other devices such as pulse generator 406, with at least one LCP capable of delivering defibrillation therapy. Still another example may include one or more LCPs implanted along with a transvenous pacemaker and with or without an implanted SICD. In yet other embodiments, the configuration or placement of the medical devices, leads, and/or electrodes may be different from those depicted in FIG. 4. Accordingly, it should be recognized that numerous other medical device systems, different from system 400 depicted in FIG. 4, may be operated in accordance with techniques disclosed herein. As such, the embodiment shown in FIG. 4 should not be viewed as limiting in any way.

In some embodiments, LCP 100 may be configured to operate in one or more modes. Within each mode, LCP 100 may operate in a somewhat different manner. For instance, in a first mode, LCP 100 may be configured to sense certain signals and/or determine certain parameters from the sensed signals. In a second mode, LCP 100 may be configured to sense at least some different signals and/or determine at least some different parameters than in the first mode. In at least one mode, LCP 100 may be configured to determine a respiration pattern of a patient and/or a posture of the patient and modulate delivery of electrical stimulation therapy based on the determined respiration pattern and/or posture of the patient. For ease of description, a mode that includes LCP 100 being configured to determine a respiration pattern of a patient and modulate delivery of electrical stimulation therapy based on the determined respiration pattern and/or posture of the patient may be called a sinus arrhythmia mode. Other modes may include one or more programming and/or therapy modes, and it may be possible for LCP 100 to be engaged in multiple modes concurrently.

In some embodiments, LCP 100 may include a therapy mode where LCP 100 operates as a pacemaker and delivers electrical stimulation therapy, such as electrical stimulation pulses, to a heart to drive a specific heart rate for the patient. LCP 100 may be configured to modulate the rate at which LCP 100 delivers electrical stimulation therapy in order to drive different heart rates for the patient. For instance, LCP 100 may configured to deliver electrical stimulation in a rate-adaptive manner, as described previously. In at least some of these embodiments, LCP 100 may additionally include a sinus arrhythmia mode, which may be a specific therapy mode or may modify a therapy mode. In the sinus arrhythmia mode, LCP 100 may modulate the rate of delivery of electrical stimulation therapy based on a determined respiration pattern and/or a posture of the patient.

When LCP 100 is in a sinus arrhythmia mode, LCP 100 may be configured to sense one or more different signals, or sense one or more signals in a different manner, than when not in a sinus arrhythmia mode. As one example, when not in a sinus arrhythmia mode, LCP 100 may be configured to sense signals generated by an accelerometer of mechanical sensing module 108 at first time periods in relation to a cardiac cycle. When in a sinus arrhythmia mode, LCP 100 may be configured to sense the generated accelerometer signals at different or additional time periods in relation to a cardiac cycle, or to sense the generated accelerometer signal using a higher sampling rate, than when not in a sinus arrhythmia mode. In other embodiments, when in a sinus arrhythmia mode, LCP 100 may be configured to process sensed signals in a different or additional manner than when not in a sinus arrhythmia mode. For instance, when in a sinus arrhythmia mode, LCP 100 may be configured to determine one or more parameters, such as a respiration pattern, based on a sensed signal that LCP 100 is not configured to determine when not in a sinus arrhythmia mode.

When part of a system, LCP 100 may enter a sinus arrhythmia mode based on a signal communicated from another device, for example external support device 420 or pulse generator 406. In other embodiments, LCP 100 may be configured to enter a sinus arrhythmia mode periodically. For instance, LCP 100 may be configured to enter a sinus arrhythmia mode once a day or once a week at a predetermined time, such as when the patient is sleeping. In still other embodiments, LCP 100 may be configured to enter a sinus arrhythmia mode based on one or more characteristics of a sensed signal, as will be described in more detail below.

As mentioned, when in a sinus arrhythmia mode, LCP 100 may be configured to determine a respiration pattern. For example, LCP 100 may be configured to sense one or more signals (e.g. accelerometer signals, transthoracic impedance signals, intracardiac impedance etc.) and determine a respiration pattern, possibly based on one or more determined parameters. LCP 100 may then modulate delivery of electrical stimulation therapy, for instance such as the timing or rate of delivered electrical stimulation pulses, based on the determined respiration pattern. The following techniques describe various example ways in which LCP 100 may determine a respiration pattern and modulate delivery of electrical stimulation therapy based on the status based the determined respiration pattern.

Throughout this description, LCP 100 is described as sensing signals, determining parameters, determining a respiration pattern, and modulating delivery of electrical stimulation therapy. However, where LCP 100 is part of a system, such as system 400 as one example, the sensing of signals, determining parameters, determining a respiration pattern, and/or modulating delivery of electrical stimulation therapy may be split up in any manner between any combinations of the devices of the system. For instance, LCP 100 may sense one or more signals and communicate those signals to another device, such as pulse generator 406. Pulse generator 406, then, may determine one or more parameters or the respiration pattern based on the signals received from LCP 100. In some further embodiments, pulse generator 406 may be further configured to communicate the determined respiration pattern to LCP 100. In other embodiments, pulse generator 406 may determine a respiration pattern on its own, for instance based off of signals sensed by pulse generator 406, and communicate the respiration pattern to LCP 100. LCP 100 may then modulate delivery of electrical stimulation therapy based on the received respiration pattern. In still other embodiments, pulse generator 406 may be the device that delivers electrical stimulation therapy and, hence, modulate the delivery of the electrical stimulation therapy based on once or more signals sensed by LCP 100. These are just some examples contemplated by this disclosure of how the sensing, determining, and modulating processes may be split up amongst the devices of a system.

In some instances, the disclosed techniques may apply to devices other than leadless cardiac pacemakers. For instance, a device such as MD 200 may include a lead configured to be attached to a heart wall, which in some cases may include an accelerometer in the tip of the lead. Such devices may also make use of the disclosed techniques.

In some embodiments, LCP 100 may include an accelerometer and may be configured to enter a sinus arrhythmia mode based on signals sensed from the accelerometer. For instance, LCP 100 may be configured determine a posture of the patient and/or a patient activity level and use one or both of these parameters to determine when to enter a sinus arrhythmia mode. In the embodiments described in the present disclosure, the accelerometer comprises a three-axis accelerometer, but this may not be the case in all embodiments. Other contemplated embodiments include accelerometers having one or two axes.

Figure 5:
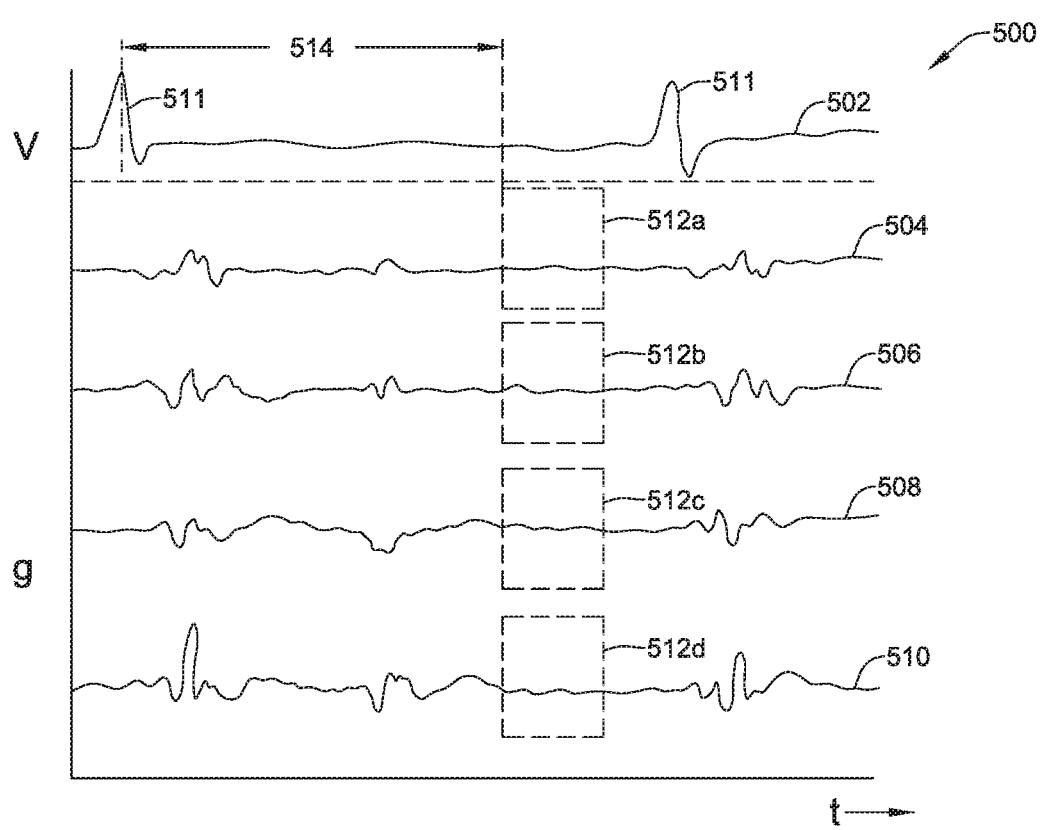
FIG. 5 depicts a graph including a cardiac electrical signal and accelerometer signal tracings shown on the same time axis.

FIG. 5 depicts graph 500 including a number of signal tracings shown on the same time axis. The signal tracings of graph 500 represent signals sensed or generated by an LCP 100 during a time period where LCP 100 is attached to a wall of a patients' heart. Signal 502 represent a cardiac electrical signal sensed by LCP 100. Signals 504, 506, and 508 represent signals from different axes generated by a three-axis accelerometer of LCP 100. Signal 510 may represent an accelerometer magnitude signal, which may be determined by summing signals 504, 506, and 508 or summing the absolute values of signals 504, 506, and 508. In other embodiments, signal 510 may represent a different signal generated by other combinations of signals 504, 506, and 508, such as a root-mean-square or root-sum-square of signals 504, 506, and 508, or any other derivation of signals 504, 506, and 508.

In some embodiments, when not in a sinus arrhythmia mode, LCP 100 may be configured to sense one or more of signals 504, 506, 508 and/or 510, or generate one or more of signals 504, 506, 508 and/or 510 via the accelerometer, during predetermined time periods. For instance, to sense signals 504, 506, 508 and/or 510, LCP 100 may be configured to receive signals 504, 506, 508 and/or 510 at processing module 110. In some embodiments, LCP 100 may connect an output of the accelerometer to processing module 110 during the time periods where LCP 100 is sensing signals 504, 506, 508 and/or 510. In other embodiments, the accelerometer may be configured to actively output signals 504, 506, 508 and/or 510 during the time periods where LCP 100 is sensing signals 504, 506, 508 and/or 510, for example using a communication link connecting processing module 110. Where processing module 110 is a digital device, sensing signals 504, 506, 508 and/or 510 may include sampling signals 504, 506, 508 and/or 510 at desired times. In other embodiments, LCP 100 may control the generation of signals 504, 506, 508 and/or 510 by the accelerometer. For instance, LCP 100 may control when power is delivered to the accelerometer, and the accelerometer may only generate signals 504, 506, 508 and/or 510 when power is delivered to the accelerometer. In some cases, LCP 100 may switch the accelerometer from a lower-power state to a higher-power state during time periods where LCP 100 desires to sense the accelerometer signal(s). During the lower-power state, the accelerometer may not provide an appreciable signal at an output for LCP 100 to sense and/or sample. As such, when LCP 100 senses a sensor signal, the sensing may include receipt of the sensor signal by processing module 110, or both the generation of the sensor signal by the sensor and receipt of the sensor signal by processing module 110.

As mentioned, LCP 100 may be configured to sense one or more signals during predetermined time periods. Such predetermined time periods may be represented by sensing periods 512a-512d in FIG. 5. Sensing periods 512a-512d may occur at regular intervals, such as every five seconds, every second, every eight hundred milliseconds, every seven hundred milliseconds, or any other suitable value. Alternatively, LCP 100 may initiate sensing periods 512a-512d after every beat, once every other beat, once every five beats, or at any other suitable frequency. In at least some cases, LCP 100 may adjust the regular interval according to a heart rate of the patient such that successive sensing periods 512a-512d occur during the same portion of the cardiac cycle (e.g. when the heart is quiet such as between heart beats).

In other embodiments, LCP 100 may implement sensing periods 512a-512d based on one or more detected features of cardiac electrical signal 502. For instance, LCP 100 may detect one or more features of cardiac electrical signal 502, such as cardiac electrical events 511. Cardiac electrical events 511 may represent R-waves or other morphological features that may be detected by LCP 100. Upon detection of a cardiac electrical event 511, LCP 100 may initiate a time period, such as time period 514. Upon expiration of time period 514, LCP 100 may initiate sensing periods 512a-512d, during which LCP 100 may sense one or more of signals 504, 506, 508 and 510. In at least some cases, LCP 100 may adjust time period 514 based on the heart rate of the patient. For instance, when the heart rate is at a relatively higher rate, LCP 100 may shorten time period 514, and when the heart rate is at a relatively lower rate, LCP 100 may lengthen time period 514. This may help to ensure that LCP 100 consistently initiates sensing periods 512a-512d during the same or similar portion of the cardiac cycle.

In some instances, the length of time period 514 may be chosen to align with a portion of the cardiac cycle where the heart is relatively mechanically inactive, such as shown in FIG. 5. For instance, time period 514 may be chosen so that it expires between about fifty milliseconds to about one-hundred fifty milliseconds before the beginning of the next heartbeat. During this portion of the cardiac cycle, the heart muscle is in a relatively relaxed state while filling with blood. Accordingly, during this portion of the cardiac cycle, the orientation of LCP 100 may be at relatively consistent position. This may allow LCP 100 to detect a posture of the patient, as explained in more detail below. In other embodiments, an accelerometer or other sensor may be implanted in the patient outside of the heart, and may transmit an indication of posture to the LCP 100.

Figure 6:
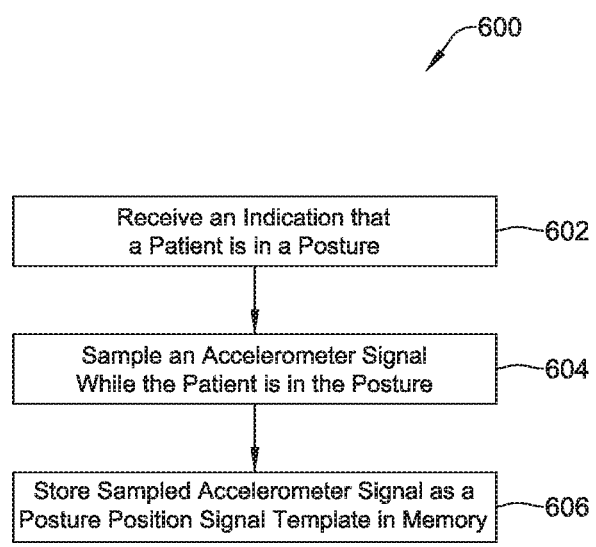
FIG. 6 depicts a flow diagram illustrating an exemplary method of programming a medical device of the present disclosure.
Figure 7:
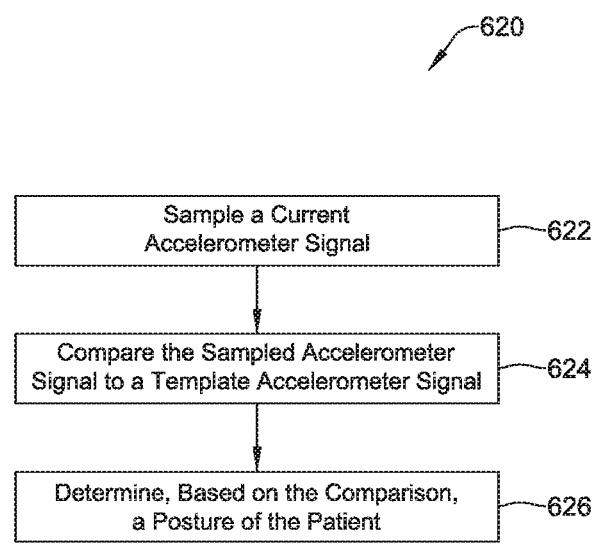
FIG. 7 depicts a flow diagram illustrating an exemplary method of determining a posture.

FIGS. 6 and 7 depict flow diagrams of exemplary methods of how LCP 100 can determine a posture of the patient. FIG. 6 depicts a flow diagram of method 600 of a method of how LCP 100 can be programmed according to different postures of the patient. Once LCP 100 has been implanted within a patient's heart, LCP 100 may receive an indication that the patient is in a defined posture, as shown at 602. For instance, the patient may be positioned in an upright posture, and this may be communicated to the LCP 100 via an external support device, such as external support device 420, which in some embodiments may be a device programmer.

Once LCP 100 has received the indication, LCP 100 may sample the accelerometer signal while the patient is in the posture, as shown at 604. For instance, LCP 100 may provide power to the accelerometer so that the accelerometer may generate an accelerometer signal and LCP 100 may sample the accelerometer signal for a predefined period of time while the patient is in the defined posture. In embodiments where the accelerometer is always generating an accelerometer signal, LCP 100 may simply sample the generated signal during the predefined period of time while the patient is in the defined posture.

In at least some embodiments, LCP 100 may only capture a single sample of the accelerometer signal during this programming. From this single captured sample, LCP 100 may generate a high accelerometer signal value and a low accelerometer signal value. For instance, LCP 100 may generate high and low accelerometer signal values that are about one percent, about two percent, about three percent, about five percent, about eight percent, about ten percent, or about fifteen percent, or another other suitable percentage values, higher and lower than the sampled value. LCP 100 may use these high and low accelerometer signal values as a template for the indicated posture.

Throughout this disclosure, the term 'accelerometer signal' may refer generally to one or all signals generated by the accelerometer, for example signals 504, 506, 508 and/or 510. Where LCP 100 is a three-axis accelerometer, the accelerometer may generate a signal for each of its three axes at the same time. These separate signals may be referred to as the 'accelerometer signal' herein for ease of description and the described steps or analyses may be performed on each of the signals. For instance, when LCP 100 senses or samples the accelerometer signal, LCP 100 may sense or sample each of the generated accelerometer signals. Accordingly, when LCP 100 senses the accelerometer signal during specific collection periods, such as sensing periods 512a-512d, LCP 100 may sense each of the signals representing the different axes of the accelerometer during the specific sensing periods. Similarly, where LCP 100 processes the accelerometer signal, LCP 100 may process each of the accelerometer signals in the same manner.

Once LCP 100 has sensed or sampled the accelerometer signal, LCP 100 may store the sensed or sampled accelerometer signal in memory, as shown at 606. This stored accelerometer signal may represent a template corresponding to the defined posture. In some cases, stored accelerometer signal is processed to develop an envelope and/or to extract certain features from the stored accelerometer signal to define a template that corresponds to the defined posture. This may be repeated for two or more different defined postures (e.g. an upright posture, a laying-down posture, a prone posture, a supine posture, a sitting posture, or any other suitable posture). As will be described in more detail below with regard to FIG. 7, LCP 100 may use the stored templates to determine a current posture of the patient.

Once LCP 100 has been programmed according to one or more defined postures, for instance by implementation of the illustrative method 600, LCP 100 may continually or periodically determine a current posture of the patient based on the sensed or sampled accelerometer signal of the LCP 100. FIG. 7 depicts a flow diagram of an illustrative method 620 of how LCP 100 may determine the current posture of the patient. LCP 100 may sense or sample a current accelerometer signal, as shown at 622. In some cases, LCP 100 may provide power to the accelerometer so that the accelerometer may generate an accelerometer signal, and LCP 100 may then sense or sample the accelerometer signal for a predefined time period.

LCP 100 may then compare the sensed or sampled accelerometer signal to one or more stored templates, as shown at 624. In some instances, LCP 100 may perform one or more correlation analyses, such as a cross-correlation analysis, between the sensed or sampled accelerometer signal and the one or more stored templates. For example, in a relatively simple approach, LCP 100 may determine an absolute value of the differences between a high value of the sampled accelerometer signal and a high value of the template and/or between a low value of the sampled accelerometer signal and a low value of the template. LCP 100 may then compare these values to one or more thresholds to determine if there is a match with a stored template. This is just one example. If a match is found, LCP 100 may determine that the current posture of the patient corresponds to the posture of the matching template, as shown at 626.

In embodiments where each template comprises a high and low accelerometer signal value, LCP 100 may compare the sensed accelerometer signal to the high and low accelerometer signal values of each template. LCP 100 may then determine the current posture to be the posture corresponding to the high and low accelerometer signal values between which the current sensed accelerometer signal falls.

Alternatively, LCP 100 may implement more complicated processes to determine a current posture. As one example, where LCP 100 includes a three-axis accelerometer, LCP 100 may determine vector differences between the current sensed accelerometer signal and each of the posture templates, which also comprise vectors. LCP 100 may then determine an absolute value of the difference between the current sensed accelerometer signal vector and a template vector (e.g. the sum of the absolute differences in the values of each of the three channels) and compare this difference to a threshold. If LCP 100 determines that this difference for a given posture template is less than a threshold difference, then LCP 100 determines the current posture is the given posture. In alternative examples, LCP 100 may use other values, such as the sum square distances of the vectors to determine posture.

In still other alternative embodiments, LCP 100 may use other comparisons or processes than simple differences between the vectors. Rather, LCP 100 may use other general ways of comparing the vectors, such as using ratios or rolling average trending, or the like.

Further, LCP 100 may use combinations of less than all of the available channels to determine posture. For instance, LCP 100 may only use two of the three channels to determine a current posture, rather than all available channels.

In general, LCP 100 may use method 620 to determine the posture of the patient once every minute, once every 5 minutes, once every ten minutes, once every thirty minutes, once every hour, once every two hours, once every three hours, or another other suitable time period. Alternatively, LCP 100 may determine the posture of the patient every heartbeat, every other heartbeat, every five heartbeats, or at any other suitable frequency.

Alternatively, or in addition, LCP 100 may determine the posture of the patient based on one or more thresholds corresponding to the heart rate of the patient, for example if the heart rate rises above or falls below a heart rate threshold. Alternatively, or in addition, LCP 100 may be configured to determine the posture of the patient based on one or more messages received from another device external to LCP 100. For instances, another LCP, an SICD, sensor or any other external device may sense the posture of the patient and send a message indicating the sensed posture to the LCP 100. These are just a few examples of other methods by which LCP 100 may determine the posture of the patient. It is contemplated that LCP 100 may use more than one of these example techniques, and any combination of these or other techniques, to determine and/or verify the current posture of the patient.

LCP 100 may be configured to determine the posture of the patient, as described above, and/or to detect when the patient has changed postures. In some embodiments, LCP 100 may monitor the posture of the patient to determine when to switch into the sinus arrhythmia mode described above. For instance, LCP 100 may be configured to enter the sinus arrhythmia mode after determining that the patient is in a sleep posture. In some instances, the sleep posture may include a laying-down posture, a prone posture, and/or a supine posture. In other instances, LCP 100 may determine that the patient is in the sleep posture after LCP 100 has determined that the patient has been in the laying-down posture, the supine posture, the prone posture, and/or any combination of these postures, for at least a threshold amount of time. As one example, LCP 100 may be configured to begin a timer after detecting that the patient is in the laying-down posture, the supine posture, and/or the prone posture. LCP 100 may then determine that the patient is in the sleep posture if the timer expires before LCP 100 determines that the patient is no longer in the laying-down posture, the supine posture, and/or the prone posture.

In some instances, LCP 100 may use other signals in conjunction with determining that the patient is in a sleep posture to determine when to enter the sinus arrhythmia mode. As one example, LCP 100 may track a patient activity level using the accelerometer. To determine the patient activity level, LCP 100 may determine a difference between the sampled current accelerometer signal and a previously sampled accelerometer signal. LCP 100 may generate an activity parameter based on this determined difference. In other embodiments, LCP 100 may store the determined difference and may generate new determined differences on a rolling basis as LCP 100 samples new current accelerometer signals. LCP 100 may determine a patient activity level from multiple of these determined differences. For instance, LCP 100 may sum the differences together to produce a patient activity parameter. LCP 100 may then compare the patient activity parameter to one or more thresholds to determine the activity level of the patient. In general, low patient activity levels may indicate relatively little patient activity or movement as the difference between the sampled current accelerometer signal and the previously sampled accelerometer signal are small. Likewise, larger determined differences may indicate relatively greater patient activity or movement. Where LCP 100 is configured to track a patient activity level, LCP 100 may be configured to enter the sinus arrhythmia mode only after detecting that the patient is in the sleep posture in addition to determining that the patient activity parameter is under a threshold amount of patient activity, or has been under a threshold amount of patient activity for at least a predetermined period of time.

Figure 8:
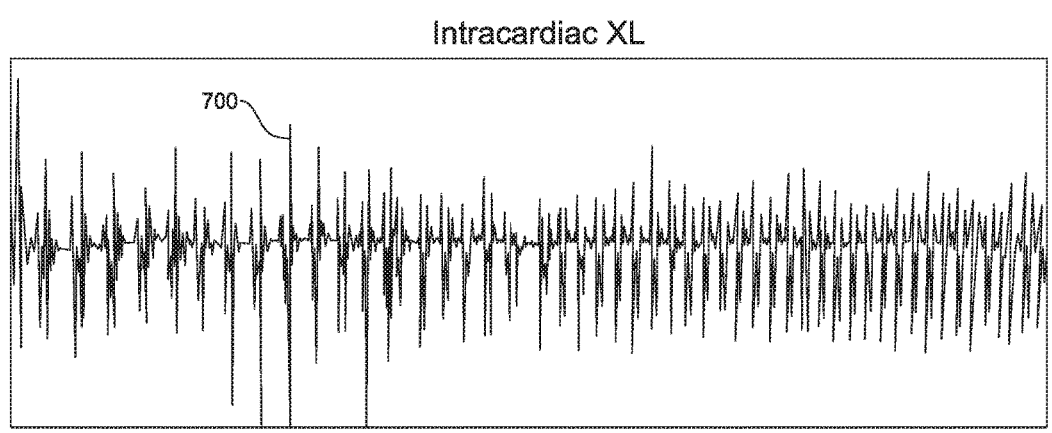
FIG. 8 depicts a graph of illustrative raw accelerometer data plotted over a number of cardiac cycles.
Figure 9:
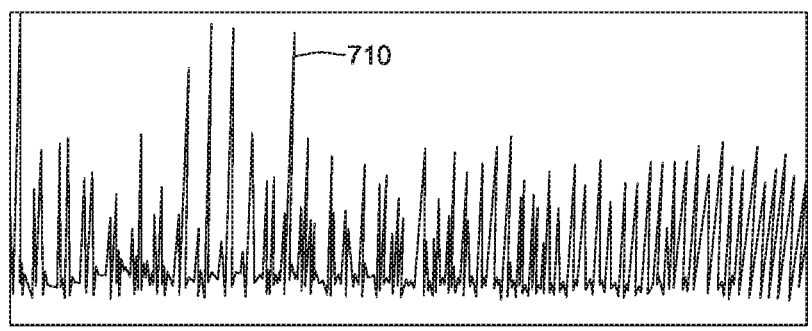
FIG. 9 depicts a graph of the absolute value of the illustrative raw accelerometer data of FIG. 8.
Figure 10:
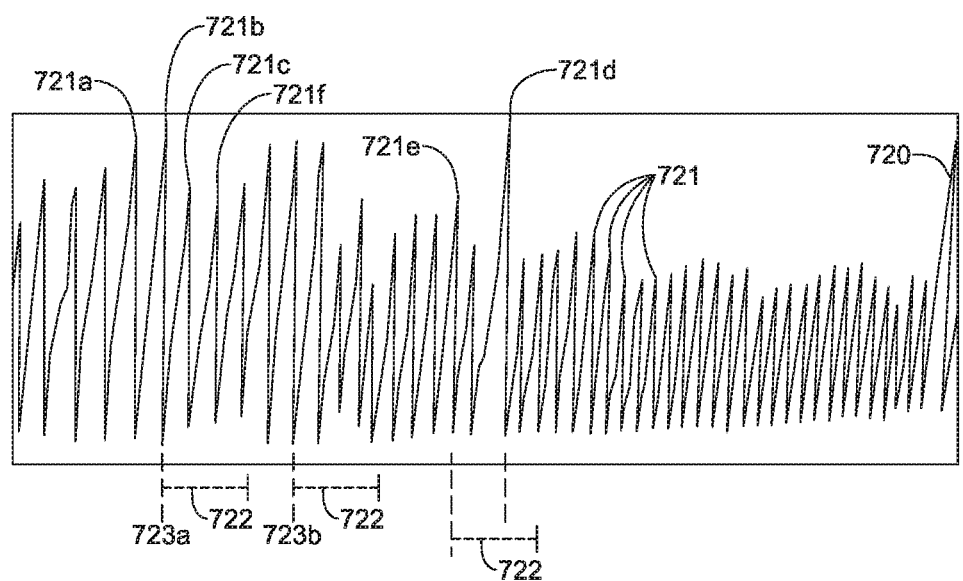
FIG. 10 depicts a graph of an integrated signal based on the absolute value of the illustrative raw accelerometer data of FIG. 9.

In some cases, once LCP 100 enters the sinus arrhythmia mode, LCP 100 may adjust how the accelerometer signal is sensed. For instance, LCP 100 may be configured to sense the accelerometer signal for longer time periods in a sinus arrhythmia mode than when not in the sinus arrhythmia mode. Additionally, or alternatively, LCP 100 may sample the accelerometer signal at a higher sample rate and/or may increase the length of the sensing periods during which LCP 100 senses or samples the accelerometer signal. In at least some embodiments, LCP 100 may be configured to sense the accelerometer signal substantially continuously when in the sinus arrhythmia mode. In some cases, and based on this differently sensed accelerometer signal, LCP 100 may determine a respiration pattern of the patient. FIGS. 8-10 depict example accelerometer signals and example processed accelerometer signals detailing one illustrative way in which LCP 100 may determine a respiration pattern of the patient.

FIG. 8 depicts raw accelerometer data 700 taken over a period of time. In this instance, raw accelerometer data 700 represents accelerometer data captured, e.g. sensed or sampled, over a number of cardiac cycles. Raw accelerometer data 700 may represent a signal output from the accelerometer of LCP 100 when LCP 100 is attached to a heart wall.

To determine a respiration pattern, LCP 100 may process raw accelerometer data 700 in any suitable manner. In at least some examples, LCP 100 may begin by determining an absolute value of raw accelerometer data 700, as shown in FIG. 9 and represented by absolute value data 710. Thereafter, LCP 100 may determine an integrated signal, or integral, of the absolute value data 710. In some instances, LCP 100 may determine the integrated signal of absolute value data 710 over each cardiac cycle. LCP 100 may identify each cardiac cycle based on, for example, the positioning of R-wave peaks. Integrated signal 720 of FIG. 10 depicts what such an integrated signal of absolute value data 710 may look like.

After determining integrated signal 720, LCP 100 may determine a respiration pattern directly from integrated signal 720. In at least some embodiments, the respiration pattern may be a respiration rate. As one example, LCP 100 may determine beginning exhalation times, identified as beginning exhalation times 723*a-b*, which represent a change in a respiratory phase. The beginning exhalation times represent changes in the respiratory phase from inhalation to exhalation and further may mark the beginning of an exhalation period.

To find beginning exhalation times 723*a-b*, LCP 100 may determine which of peaks 721 of integrated signal 720 represent local maximums. For instance, LCP 100 may determine that peak 721*b* has a greater maximum value than either of peaks 721*a* or 721*c*, which occur just prior to 721*b* and just subsequent to peak 721*b* respectively. Accordingly, LCP 100 may determine that a beginning of an exhalation occurs at time 723*a*, which is in alignment with peak 721*b*. Using a similar methodology, LCP 100 may determine the beginning of another exhalation at time 723*b*.

LCP 100 may use the difference in times between beginning exhalation time 721*a* and beginning exhalation time 721*b* in order to determine a respiration rate. For instance, LCP 100 may divide sixty seconds by the difference in time between two successive beginning exhalation times, such as times 723*a* and 723*b*. As one numerical example, if times 723*a* and 723*b* are two seconds apart, LCP 100 may determine the respiration rate to be 30 breaths per minute. Of course, in other examples, LCP 100 may determine a respiration rate based on identified local minimums representing beginning inhalation times. These beginning inhalation times represent a change in a respiratory phase from exhalation to inhalation and may further mark the beginning of an inhalation period. LCP 100 may determine times of local minimums in a similar manner to how LCP 100 may determine local maximums, except LCP 100 may identify peaks that have lower values than other nearby peaks. In some further embodiments, LCP 100 may use the determined respiration rate to predict future timings of the beginning of inhalations and/or exhalations.

In still other embodiments, the respiration pattern may include periods of inhalation and periods of exhalation. For instance, as described, beginning timings of exhalation and inhalation may mark the beginning of exhalation and inhalation periods, respectively. Accordingly, LCP 100 may determine beginnings and endings of exhalation and inhalation periods and may modulate the delivery of electrical stimulation based on these determined periods.

In some additional or alternative embodiments, LCP 100 may employ one or more enhancements to the method described above. For instance, LCP 100 may only determine that a peak 721 that correspond to a local maximum also corresponds to a beginning exhalation time if the identified peak is not within a threshold time of the previous peak determined to be a local maximum. For instance, looking at integrated signal 720, although peak 721*d* is a local maximum, peak 721*d* occurs within blanking period 722 of local maximum peak 721*e*. Accordingly, LCP 100 may not consider peak 721*d* as corresponding to a beginning exhalation time. LCP 100 may reset blanking period 722 after each determination of a beginning exhalation time. Blanking period 722 may help smooth out the determined respiration rate and help ensure that the respiration rate is not significantly affected by artifacts that affect the accelerometer signal from sources other than inhalation and exhalation. In some cases, blanking period 722 may range anywhere from one-quarter of a second to one second or more. In some instances, LCP 100 may adjust blanking period 722 based on the last known good respiration rate or an expected respiration rate. Additionally, in some instances, LCP 100 may adjust blanking period 722, for example, based on one or more other sensed signals. The blanking period 722 may also be adjusted down as the respiration rate increases, and visa-versa.

In some examples, LCP 100 may determine an overall respiration rate that is a rolling average of five respiration rates determined by the difference in timings of five successive pairs of beginning exhalation (or inhalation) times. However, the exact number of respiration rates used to determine the overall respiration rate may differ in other embodiments. In alternative cases, the overall respiration rate may be the most recent determined respiration rate. These are just some examples of how LCP 100 may determine a respiration rate based on integrated signal 720.

Figure 11:
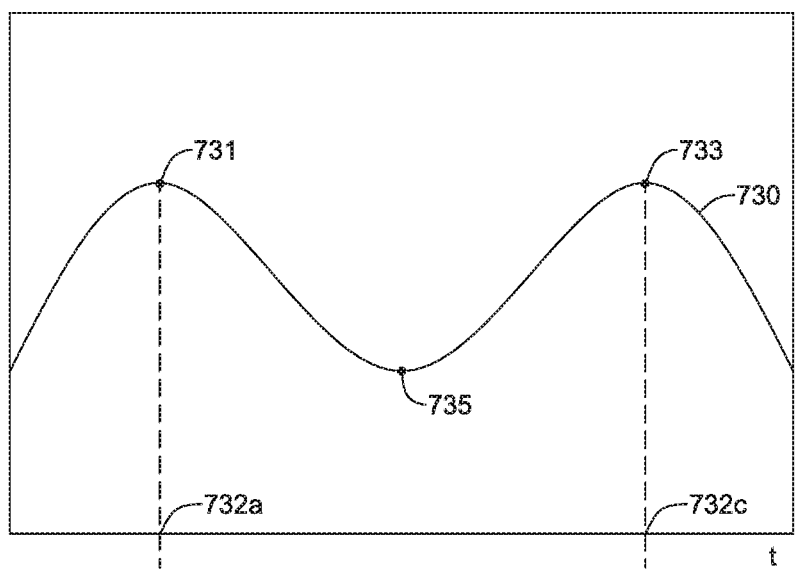
FIG. 11 depicts a graph of a low-pass filtered signal generated by low pass-filtering the integrated signal of FIG. 10.

In some alternative or additional embodiments, LCP 100 may further process integrated signal 720 in order to determine or produce a respiration pattern. In these embodiments, LCP 100 may pass integrated signal 720 through a low pass filter. An illustrative filtered signal 730, shown in FIG. 11, represents an output after low-pass filtering integrated signal 720. As one example, LCP 100 may determine timings of the inflections of filtered signal 730 by taking the first derivative of filtered signal 730 and finding the zero-crossings. Then, the differences in timings between zero-crossing, represented by peaks and valleys in filtered signal 730 may be used to determine a respiration rate. For example, LCP 100 may take the difference in timing between time 732a and time 732c, and divide sixty by the resulting difference to determine a respiration rate in breaths per minute.

In some alternative embodiments, the respiration pattern may be represented by a signal rather than a respiration rate. For instance, in some embodiments, the respiration pattern may comprise filtered signal 730. LCP 100 may be able to detect the peaks and valleys of signal 730, for examples peaks 731 and 733 and valley 735, which may represent changes from inhalation to exhalation and from exhalation to inhalation. In other embodiments, the respiration pattern may comprise a signal other than filtered signal 730. For instance, raw accelerometer data 700 may be processed in a different manner than described with respect to FIGS. 8-10. As one example, LCP 100 may apply a low pass filter directly to raw accelerometer data 700. LCP 100 may use a filter that has a corner frequency of, for example, between 0.3 Hz and 0.7 Hz, and in some examples, LCP 100 may use a filter with a corner frequency of 0.5 Hz. In such embodiments, the resulting filtered signal may look similar to filtered signal 730. Where the respiration pattern is a signal, LCP 100 may modulate the delivered electrical stimulation therapy based on the peaks and valleys in the respiration pattern.

It should be understood that although the above description revolved around determining a respiration pattern based on accelerometer data, other signals can be used to determine a respiration pattern. For instance, LCP 100 may use ECG data to determine a respiration pattern. When LCP 100 is implanted within a chamber of the heart, LCP 100 may sense intracardiac electrical signals, for example represented by an ECG, via a sense amplifier or the like. The relative magnitude of the R-wave of the ECG signal may fluctuate with changes in the volume of the heart chamber, and the volume of the heart chamber may fluctuate as a function of intrathoracic pressure—such as due to changes in lung volume of the patient due to respiration. In some instances, such changes in intracardiac pressure may be used to determine the respiration pattern, such as a respiration rate. Alternatively or additionally, the intracardiac signals may be processed in order to determine a signal representing the respiration pattern.

In some cases, LCP 100 may include a pressure sensor and/or a flow sensor and may sense the intra-chamber blood pressure and/or blood flow. An intra-chamber blood pressure signal and/or blood flow signal generated by a corresponding sensor may vary with respiration of the patient. For instance, intra-chamber blood pressure and/or blood flow signals may be relatively lower during inspiration and relatively higher during expiration during the same portion of the cardiac cycle. Accordingly, LCP 100 may process the generated intra-chamber blood pressure signal and/or blood flow signal to determine a respiration pattern.

In some instances, instead of determining a respiration pattern based solely on signals sensed by LCP 100, LCP 100 may receive an indication of a respiration pattern from another device. The other device may be configured to determine a respiration pattern, as one example, through intra-thoracic impedance measurements. As lungs of the patient fill with air during inhalation, the determined intra-thoracic impedance may increase. The intra-thoracic impedance may fall as air is expelled from the lungs during exhalation. Accordingly, the external device may communicate the determined intra-thoracic impedances to LCP 100, and LCP 100 may determine a respiration pattern from the communicated signals. In alternative embodiments, the external device may determine the respiration pattern and communicate the determined respiration pattern to LCP 100.

Accordingly, using any of the above described techniques or combination of the above techniques, LCP 100 may determine a respiration pattern. During periods of exhalation, for instance between peak 731 and valley 735, pressure exerted by the lungs and the diaphragm on the heart may decrease relative to periods of inhalation, for instance between valley 735 and peak 733. As such, during periods of exhalation, the heart of the patient may be able to relax to a greater extent than during periods of inhalation. This may allow for greater filling of the heart and, hence, greater cardiac output. In some instances, it may be beneficial to the patient for LCP 100 to slow the heart rate during periods of exhalation in order to give the heart greater rest, as cardiac output may still be maintained even at the lower heart rate due to the greater filling during these exhalation periods.

As such, it is contemplated that when in the sinus arrhythmia mode, LCP 100 may be configured to deliver electrical stimulation therapy at a slower rate during periods of exhalation than during periods of inhalation. In some instances, LCP 100 may deliver electrical stimulation pulses at a rate that is about 1 pulse per minute slower when LCP 100 determines that the patient is in an exhalation period than when the patient is in an inhalation period. In other embodiments, the rate difference may be about 2 pulses per minute, about 3 pulses per minute, about 4 pulses per minute, or any other suitable rate difference. This value may be programmable, and/or may be dynamic. For instance, at relatively higher heart rates, the differences between the slower rate and the higher rate may be less than for relatively lower heart rates.

In some cases LCP 100 may be governed by a lower rate limit (LRL), which is a lowest rate at which LCP 100 may deliver electrical stimulation pulses under normal conditions. In some embodiments where LCP 100 includes a sinus arrhythmia mode, LCP 100 may be permitted to adjust the rate of delivered electrical stimulation pulses below the LRL, for instance during periods of exhalation. Or, alternatively, LCP 100 may simply modulate the LRL during the periods of exhalation to achieve a lower rate of delivery of electrical stimulation pulses.

As one example, LCP 100 may monitor the respiration pattern for peaks and valleys, such as peaks 731 and 733 and valley 735. Upon detection of a peak or valley, LCP 100 may change the rate of delivery of electrical stimulation pulses. For instance, once LCP 100 detects valley 735, LCP 100 may switch to delivering electrical stimulation pulses at a faster rate. Then, once LCP 100 detects peak 733, LCP 100 may switch to delivering electrical stimulation pulses at a slower rate.

In some cases, LCP 100 may begin a timer upon detecting a peak or valley and may switch delivery rates based upon expiration of the timer. The length of the timer may be related to a determined respiration rate that LCP 100 may determine from the respiration pattern. In some instances, the length of the timer may be generally chosen to expire about halfway to the next expected peak or valley, as determined based on the respiration rate. The LCP 100 may then turn off or switch the accelerometer to a lower power inactive mode, and rely on the timer to align the switching of delivery rates to the patients' respiration cycle. From time to time, the LCP 100 may turn on or switch the accelerometer back to a higher power active mode to check and/or realign the timer with the patients' respiration cycle. This may help reduce the power that is consumed by the LCP by only activating the accelerometer intermittently.

In some instances, LCP 100 may change the rate of delivery of electrical stimulation pulses based on a determine respiration rate. For instance, as described, LCP 100 may determine a respiration rate based on beginning exhalation times and/or beginning inhalation times. After determining the respiration rate, LCP 100 may change the rate of delivery of electrical stimulation pulses to a rate that is twice the respiration rate. As one numerical example, if LCP 100 determines that the respiration rate is fifteen breaths per minute, LCP 100 may change the rate of delivery of electrical stimulation pulses once every two seconds. In these embodiments, LCP 100 may begin changing the rate of delivery of electrical stimulation pulses upon a determination of a beginning exhalation time or beginning inhalation time so that the changes in the rate of delivery of electrical stimulation pulses correspond with changes from exhalation to inhalation and inhalation to exhalation.

In some alternative embodiments, instead of having binary electrical stimulation pulse delivery rates, e.g. a higher rate and a lower rate, LCP 100 may slowly decrease or increase the rate of delivery of the electrical stimulation pulses. For example, LCP 100 may begin lowering the rate of delivery of electrical stimulation pulses upon detection of a peak in a respiration pattern or a beginning exhalation time. Further, LCP 100 may begin increasing the rate of delivery of electrical stimulation pulses upon detection of a valley in a respiration pattern or a beginning inhalation time. In some of these embodiments, LCP 100 may have a maximum lower rate and a maximum upper rate that bound how far LCP 100 may decrease or increase the rate of delivery of electrical stimulation pulses. For instance, when in the sinus arrhythmia mode, LCP 100 may adjust the LRL down to a lower level and, upon detection of a peak in a respiration pattern or a beginning exhalation time, begin to decrease the rate of delivery of electrical stimulation pulses toward the lowered LRL.

Figure 12:
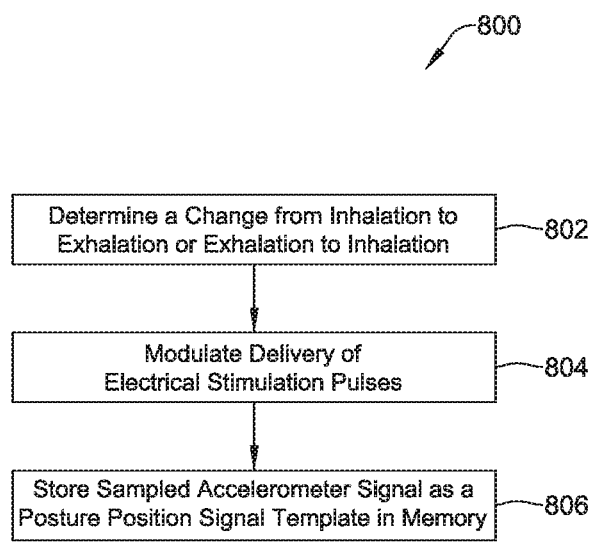
FIG. 12 depicts a flow diagram illustrating an exemplary low power method of operating a medical device of the present disclosure.

In some additional or alternative embodiments, once LCP 100 has determined the respiration pattern, LCP 100 may switch to a lower-power sinus arrhythmia mode. FIG. 12 depicts method 800, detailing one example of how LCP 100 may operate in a lower-power sinus arrhythmia mode. In general, when LCP 100 is in the lower-power sinus arrhythmia mode, LCP 100 may adjust how often LCP 100 senses the accelerometer signal. For instance, as described, when LCP 100 is in the sinus arrhythmia mode, LCP 100 may sense the accelerometer signal on a substantially continuous basis in order to determine the respiration pattern. When LCP 100 switches to the lower-power sinus arrhythmia mode, LCP 100 may reduce the length of time that LCP 100 senses the accelerometer signal.

In the example of method 800, LCP 100 may first determine a change from inhalation to exhalation or from exhalation to inhalation, as at 802. For instance, based on the sensed accelerometer signal, LCP 100 may be able to determine a peak or valley in the accelerometer signal, or a processed version of the accelerometer signal. In other instances, LCP 100 may determine a beginning exhalation time or beginning inhalation time.

After determining a change from inhalation to exhalation or from exhalation to inhalation, LCP 100 may modulate the delivery of electrical stimulation pulses, as shown at 804. For instance, LCP 100 may decrease the rate of delivery of electrical stimulation pulses if the change was from inhalation to exhalation, or increase the rate of delivery of the change was from exhalation to inhalation, as previously described.

LCP 100 may cease sensing the accelerometer signal, as shown at 806. For example, LCP 100 may cease sensing or sampling the accelerometer signal output by the accelerometer or may cause the accelerometer to cease outputting the accelerometer signal. In other embodiments, LCP 100 may cease providing power to the accelerometer so that the accelerometer no longer generates the accelerometer signal or may transition the accelerometer to the low power state.

In some instances, LCP 100 may cease sensing the accelerometer signal until just before a predicted timing of the next change from inhalation to exhalation or exhalation to inhalation. For instance, based on the determined respiration pattern, LCP 100 may predict a timing of the next change from inhalation to exhalation or exhalation to inhalation. LCP 100 may then begin sensing the accelerometer signal about fifty milliseconds, about sixty milliseconds, about seventy milliseconds, about seventy-five milliseconds, or about eighty milliseconds, or any other suitable time period, before the predicted timing of the change from inhalation to exhalation or exhalation to inhalation. Once LCP 100 detects the next change from inhalation to exhalation or exhalation to inhalation, LCP 100 may then modulate the rate of delivered electrical stimulation pulses, predict the next occurrence of a change from inhalation to exhalation or exhalation to inhalation, and once again cease sensing the accelerometer signal. In this manner, LCP 100 may save energy by not continuously sensing the accelerometer signal while in the sinus arrhythmia mode.

When so provided, LCP 100 may sense the respiration phase at discrete times, such as by detecting peaks or valleys in the respiration pattern, or by detecting beginning exhalation times or beginning inhalation times. Where LCP 100 ceases to sense the accelerometer in the low power sinus arrhythmia mode, LCP 100 may predict that the respiration phase stays the same until LCP 100 resumes actively collecting the accelerometer signal.

In some embodiments, when in the lower-power sinus arrhythmia mode, if LCP 100 does not detect a change from inhalation to exhalation or exhalation to inhalation within a predetermined time period of beginning to generate and/or sample the accelerometer signal, LCP 100 may switch back to the regular sinus arrhythmia mode. For instance, LCP 100 may switch back to actively collecting the accelerometer signal continuously to determine the respiration pattern. In some additional embodiments, LCP 100 may further switch to the higher rate of delivery of electrical stimulation pulses until LCP 100 again detects the respiration pattern or the next change from inhalation to exhalation or exhalation to inhalation.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. A method for pacing a patient's heart using a leadless cardiac pacemaker (LCP), comprising:
   a circuit of the LCP recognizing each of a plurality of R-waves and determining a sampling window following at least some of the recognized R-waves;
   sampling a signal generated by an accelerometer of the LCP during at least some of the sampling windows;
   determining, by the LCP, based at least in part on the sampled signals, that a current posture of the patient corresponds to a predetermined sleep posture, and in response, the LCP:
      determining a respiration phase of the patient based at least in part on the signal generated by the accelerometer of the LCP;
      pacing the patient's heart at a pacing rate that is modulated based at least in part on the determined respiration phase of the patient; and
   determining, by the LCP, based at least in part on the sampled signals, that the current posture of the patient does not correspond to the predetermined sleep posture, and in response the LCP:
   pacing the patient's heart at a pacing rate that is not dependent on the respiration phase of the patient.

2. The method of claim 1, wherein the current posture of the patient is determined based at least in part on a template, wherein one or more sampled signals generated by the accelerometer of the LCP during one or more sampling windows are compared to the template, and if there is a match, the patient is determined to be in the predetermined sleep posture.

3. The method of claim 1, wherein the respiration phase of the patient is determined based at least in part on a measure related to a transthoracic impedance of the patient.

4. The method of claim 1, wherein the respiration phase of the patient is determined based at least in part on a measure sensed by a flow sensor.

5. The method of claim 1, wherein the respiration phase of the patient is determined based at least in part on a measure sensed by a pressure sensor.

6. The method of claim 1, wherein the respiration phase of the patient is sensed using the accelerometer by detecting a cyclical pattern in a plurality of discrete samples each taken by the accelerometer at times when the acceleration due to cardiac motion is expected to be low.

7. The method of claim 1, further comprising modulating a lower rate limit (LRL) of the pacing rate based on the determined respiration phase of the patient when the determined posture corresponds to the predetermined sleep posture.

8. A method for pacing a patient's heart with a leadless cardiac pacemaker, comprising:
   determining, based at least in part on a signal generated by an accelerometer of the leadless cardiac pacemaker, that a current posture of the patient corresponds to a predetermined sleep posture, and in response:
      determining, based at least in part on the signal generated by the accelerometer of the leadless cardiac pacemaker, a signal indicative of a respiration pattern of a patient; and
      modulating, by the leadless cardiac pacemaker, a rate of delivery of electrical stimulation pulses to the patient's heart based at least in part on the signal indicative of the respiration pattern
   determining, based at least in part on a signal generated by the accelerometer of the leadless cardiac pacemaker, that the current posture of the patient does not correspond to the predetermined sleep posture, and in response:
      pacing, by the leadless cardiac pacemaker, the patient's heart at a pacing rate that is not dependent on the respiration phase of the patient.

9. The method of claim 8, further comprising determining periods of inhalation and periods of exhalation based at least in part on the received signal indicative of the respiration pattern.

10. The method of claim 9, wherein modulating the rate of delivery of electrical stimulation pulses based at least in part on the signal indicative of the respiration pattern comprises delivering electrical stimulation pulses at different rates during periods of inhalation and periods of exhalation.

11. The method of claim 9, wherein the rate of delivery of electrical stimulation pulses during periods of exhalation is between about 1 pulse per minute to about 3 pulses per minute slower than during periods of inhalation.

12. A leadless cardiac pacemaker (LCP) for delivering electrical stimulation pulses to a heart of a patient, comprising:
   a plurality of electrodes;
   an accelerometer; and
   a controller connected to the plurality of electrodes and the accelerometer, the controller configured to:
      determine based at least in part on a signal generated by the accelerometer that a current posture of the patient is in a first posture, and in response:
         determine periods of inhalation and periods of exhalation of the patient based at least in part on the signal generated by the accelerometer;
         deliver electrical stimulation pulses to the heart of the patient via the plurality of electrodes;
         modulate a rate of delivery of the electrical stimulation pulses via the plurality of electrodes based at least in part on the determined periods of inhalation and periods of exhalation; and
      determine based at least in part on the signal generated by the accelerometer that the current posture of the patient is in a second posture different from the first posture, and in response:
         deliver electrical stimulation pulses to the heart of the patient via the plurality of electrodes at a rate of delivery that is not dependent on determined periods of inhalation and periods of exhalation.

13. The leadless cardiac pacemaker (LCP) of claim 12, wherein the first posture corresponds to a predetermined sleep posture.

* * * * *